United States Patent
Shimamoto

(10) Patent No.: US 10,356,287 B2
(45) Date of Patent: Jul. 16, 2019

(54) OPTICAL SCANNING APPARATUS AND METHOD OF CONTROLLING OPTICAL SCANNING APPARATUS

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/910,088

(22) Filed: Mar. 2, 2018

(65) Prior Publication Data

US 2018/0191926 A1 Jul. 5, 2018

Related U.S. Application Data

(63) Continuation of application No. PCT/JP2015/079990, filed on Oct. 23, 2015.

(51) Int. Cl.

| H04N 3/34 | (2006.01) |
|---|---|
| A61B 1/00 | (2006.01) |
| A61B 1/04 | (2006.01) |
| A61B 1/07 | (2006.01) |
| G02B 23/26 | (2006.01) |
| G02B 23/24 | (2006.01) |
| G02B 26/10 | (2006.01) |

(52) U.S. Cl.
CPC ........... *H04N 3/34* (2013.01); *A61B 1/00006* (2013.01); *A61B 1/00172* (2013.01); *A61B 1/043* (2013.01); *A61B 1/07* (2013.01); *G02B 23/2469* (2013.01); *G02B 23/26* (2013.01); *G02B 26/103* (2013.01)

(58) Field of Classification Search
CPC .... H04N 3/34; A61B 1/00006; A61B 1/00172
USPC .......................................................... 348/68
See application file for complete search history.

(56) References Cited

U.S. PATENT DOCUMENTS

2010/0157037 A1\* 6/2010 Iketani ............... A61B 1/00009
348/68

FOREIGN PATENT DOCUMENTS

| JP | 2010-142597 A | 7/2010 |
|---|---|---|
| JP | 2012-231911 A | 11/2012 |
| JP | 5190267 B2 | 4/2013 |
| WO | WO 2006/041452 A1 | 4/2006 |

OTHER PUBLICATIONS

International Search Report dated Nov. 24, 2015 issued in PCT/JP2015/079990.

\* cited by examiner

*Primary Examiner* — Jeffery A Williams
(74) *Attorney, Agent, or Firm* — Scully, Scott, Murphy & Presser, P.C.

(57) ABSTRACT

An optical scanning apparatus includes an optical fiber that emits illumination light from a distal end thereof toward a subject, an actuator that oscillates the distal end of the optical fiber, and a controller that controls the actuator so as to two-dimensionally scan the illumination light on the subject and so as to satisfy Conditional Expression of $P1 \leq 0.5 \times D$, where D is a spot diameter of the illumination light on the subject, and P1 is a scanning-line pitch of the illumination light on the subject.

19 Claims, 11 Drawing Sheets

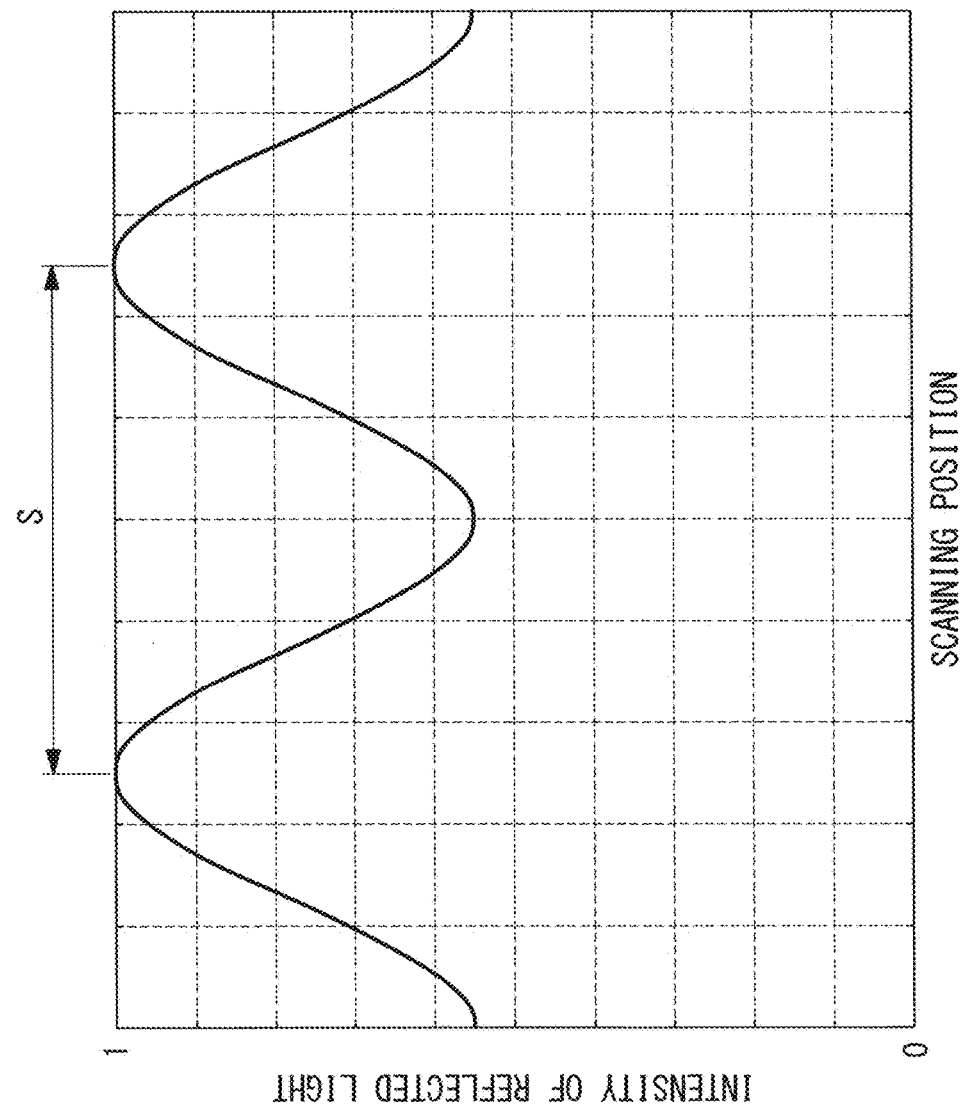

OPTICAL SCANNING APPARATUS AND METHOD OF CONTROLLING OPTICAL SCANNING APPARATUS

CROSS-REFERENCE TO RELATED APPLICATIONS

This is a continuation of International Application PCT/JP2015/079990 which is hereby incorporated by reference herein in its entirety.

TECHNICAL FIELD

The present invention relates to an optical scanning apparatus and a method of controlling the optical scanning apparatus.

BACKGROUND ART

A known scanning endoscope apparatus in the related art scans a laser beam along a spiral path (for example, see Patent Literature 1). The resolution of images captured by the scanning endoscope apparatus depends on the distance between scanning lines of the laser beam (the scanning-line pitch). In Patent Literature 1, the resolution of the images is increased by doubling the spiral number (number of circulations) of the laser beam to halve the scanning-line pitch.

CITATION LIST

Patent Literature

{PTL 1} Japanese Unexamined Patent Application, Publication No. 2010-142597

SUMMARY OF INVENTION

An optical scanning apparatus according to a first aspect of the present invention includes: an optical fiber that emits illumination light from a distal end thereof toward a subject; an actuator that oscillates the distal end of the optical fiber; and a controller that controls the actuator so as to two-dimensionally scan the illumination light emitted from the distal end of the optical fiber on the subject. The controller controls the actuator so as to satisfy Conditional Expression (1) below:

$$P1 \leq 0.5 \times D, \quad (1)$$

where D is a spot diameter of the illumination light on the subject, and P1 is a scanning-line pitch of the illumination light on the subject.

An optical scanning apparatus according to a second aspect includes: an optical fiber that emits illumination light from a distal end thereof toward a subject; an actuator that oscillates the distal end of the optical fiber; a controller that controls the actuator so as to two-dimensionally scan the illumination light emitted from the distal end of the optical fiber on the subject; and a light detecting unit that detects observation light generated in the subject as a result of the subject being irradiated with the illumination light. The controller controls the light detecting unit so as to satisfy Conditional Expression (2) below:

$$P2 \leq 0.5 \times D, \quad (2)$$

where D is a spot diameter of the illumination light on the subject, and P2 is a sampling pitch of the observation light on the subject.

A third aspect of the present invention provides a method of controlling an optical scanning apparatus that spirally scans light emitted from a distal end of an optical fiber on a subject, wherein, in a control step in which an actuator that oscillates the distal end of the optical fiber so as to two-dimensionally scan the illumination light emitted from the distal end of the optical fiber on the subject is controlled, the actuator is controlled so as to satisfy Conditional Expression (1) below:

$$P1 \leq 0.5 \times D, \quad (1)$$

where D is a spot diameter of the illumination light on the subject, and P1 is a scanning-line pitch of the illumination light on the subject.

BRIEF DESCRIPTION OF DRAWINGS

FIG. 3B is a diagram showing the distribution of the intensity of reflected light obtained when the spot diameter of the illumination light and the pitch of a stripe pattern in a chart are equal.

DESCRIPTION OF THE EMBODIMENTS

An optical scanning apparatus 1 according to an embodiment of the present invention will be described below with reference to the drawings.

Figure 1:
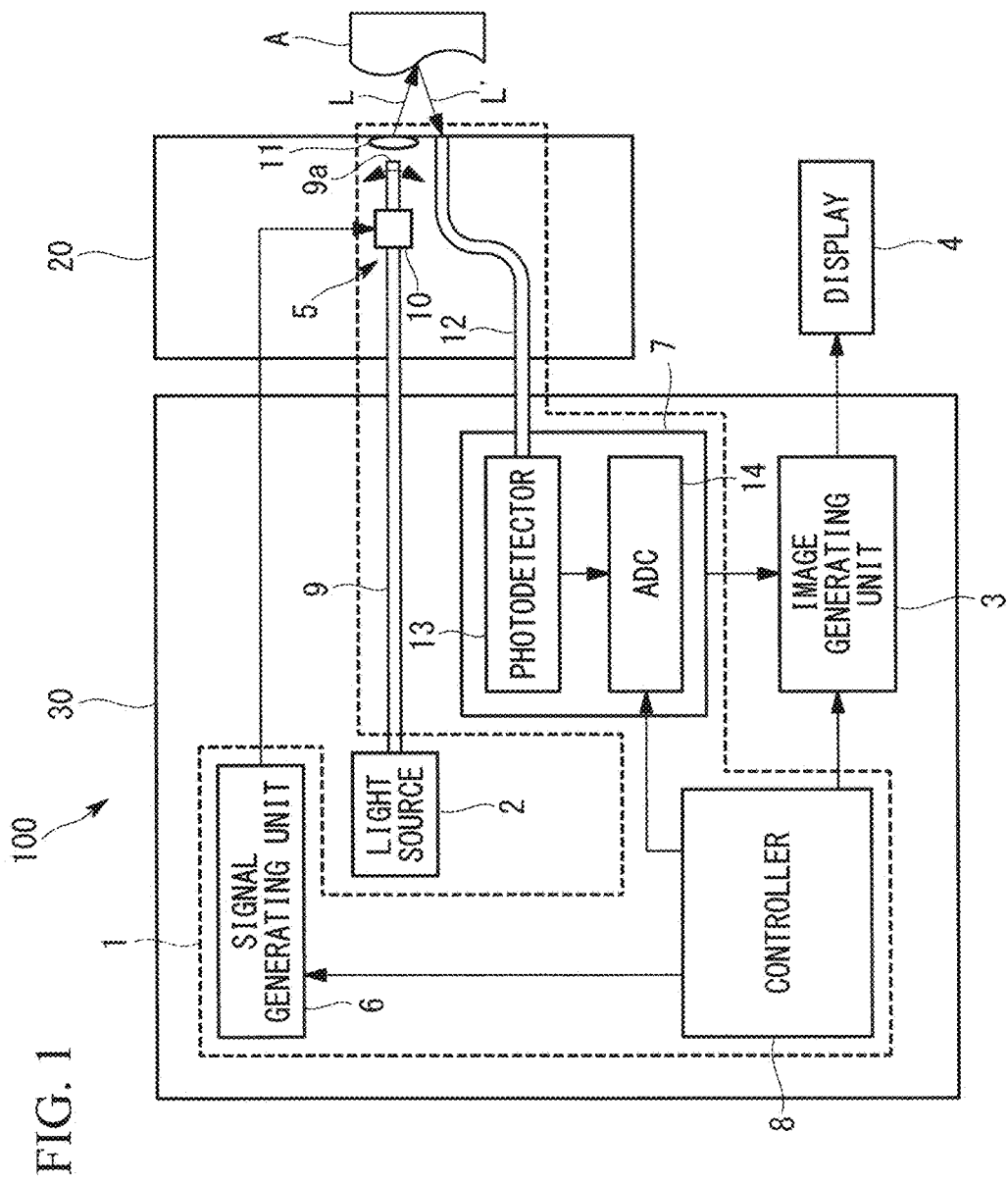
FIG. 1 shows the overall configuration of an optical scanning apparatus and a scanning endoscope system according to an embodiment of the present invention.

As shown in FIG. 1, the optical scanning apparatus 1 according to this embodiment is equipped in a scanning endoscope system 100.

The scanning endoscope system 100 includes a light source 2, the optical scanning apparatus 1 that scans illumination light L output from the light source 2 over a subject A and detects observation light L' generated in the subject A, an image generating unit 3 that generates a two-dimensional image of the subject A based on the intensity of the observation light L' detected by the optical scanning apparatus 1, and a display 4 that displays the image generated by the image generating unit 3. The observation light L' is reflected light, scattered light, or fluorescence from the subject A. Denoted by reference sign 20 is an elongated insertion section insertable into the body, and denoted by reference sign 30 is a control unit body connected to the proximal end of the insertion section 20.

The light source 2 is a laser light source that outputs a laser beam, serving as the illumination light L.

The optical scanning apparatus 1 includes an optical scanning unit 5 that scans the illumination light L from the light source 2, a signal generating unit 6 that generates a driving signal for driving the optical scanning unit 5, a light detecting unit 7 that detects the observation light L' generated in the subject A irradiated with the illumination light L, and a controller 8 for controlling the optical scanning unit 5, the signal generating unit 6, and the light detecting unit 7.

The optical scanning unit 5 includes: an optical fiber 9 that guides the illumination light L emitted from the light source 2 and entering from the proximal end thereof and emits the light from a distal end 9a thereof; an actuator 10 that oscillates the distal end 9a of the optical fiber 9 in the radial direction of the optical fiber 9; and a scanning lens system 11.

The optical fiber 9 is disposed in the insertion section 20 along the longitudinal direction thereof.

Figure 2:
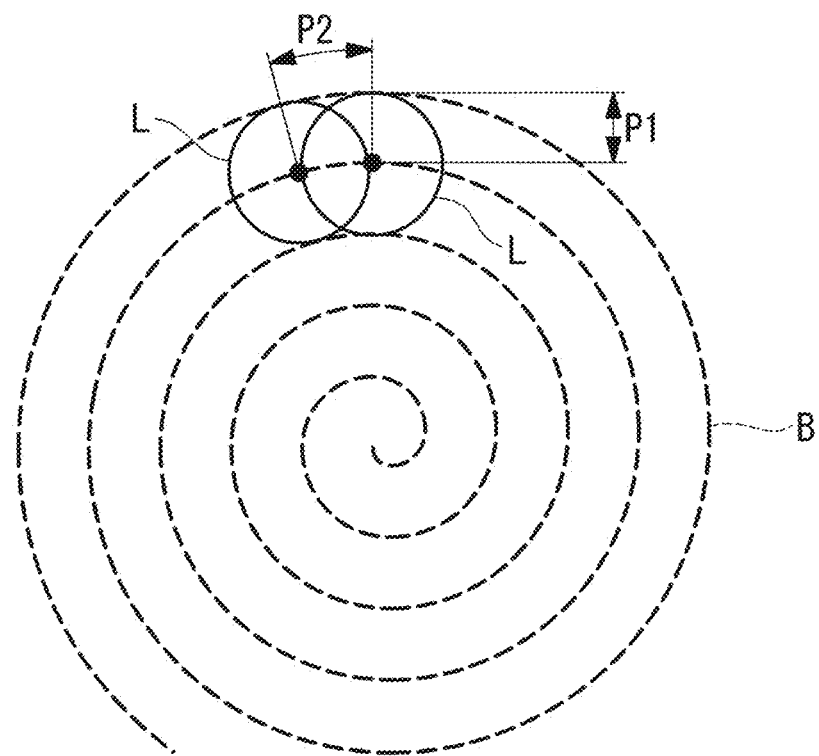
FIG. 2 is a diagram showing a scanning path, on a subject, of illumination light scanned by the optical scanning apparatus in FIG. 1.

The actuator 10 is of a piezoelectric type and is provided on the outer circumferential surface of the optical fiber 9, at a position away from the distal end 9a toward the proximal end. The actuator 10 supports one end of the distal end portion of the optical fiber 9. The actuator 10 excites an oscillation in the distal end portion of the optical fiber 9 based on a driving signal supplied from the signal generating unit 6 to spirally oscillate the distal end 9a along a spiral path. As a result, as shown in FIG. 2, the illumination light L emitted from the distal end 9a of the optical fiber 9 is spirally scanned along a spiral scanning path B over the subject A, which is opposite the distal end of the insertion section 20.

More specifically, the actuator 10 includes an X-direction piezoelectric element (not shown) and a Y-direction piezoelectric element (not shown) that oscillates the distal end portion of the optical fiber 9 in the X direction and the Y direction via, for example, a ferrule. The X direction and the Y direction are perpendicular to the longitudinal direction of the optical fiber 9 and are perpendicular to each other. The piezoelectric elements are each supplied with a high-frequency signal (continuous-wave signal), serving as a driving signal, in which gradual increase and decrease in the amplitude are repeated.

The X-direction and Y-direction piezoelectric elements having received the driving signals generate, in the distal end portion of the optical fiber 9, bending vibrations in the X direction and the Y direction, respectively, having substantially the same frequencies as the frequencies of the driving signals and having amplitudes that vary with changes in the amplitudes of the driving signals. Herein, the phase of the driving signal applied to the X-direction piezoelectric element and the phase of the driving signal applied to the Y-direction piezoelectric element are shifted from each other by substantially $\pi/2$. The application of these driving signals to the piezoelectric elements spirally oscillates the distal end 9a of the optical fiber 9.

The actuator 10 may be of an electromagnetic type in which a magnet attached to the optical fiber 9 is oscillated by means of an electromagnetic coil, or of another type, instead of the piezoelectric type.

The scanning lens system 11 is disposed in front of the distal end 9a of the optical fiber 9. The scanning lens system 11 has a positive refractive power and focuses the illumination light L entering from the distal end 9a of the optical fiber 9.

The signal generating unit 6 generates a driving signal having a frequency and amplitude specified by the control signal received from the controller 8 and supplies the driving signal to the actuator 10.

The light detecting unit 7 includes: a light-receiving optical fiber 12 that receives, at the distal end thereof, observation light L' (e.g., reflected light of the illumination light L, light scattered by the subject A, or fluorescence excited by the illumination light L) generated by the subject A; a photodetector 13, such as a photomultiplier, that detects the observation light L' received by the light-receiving optical fiber 12; and an AD converter 14 that performs analog-to-digital (AD) conversion of the electric signal output from the photodetector 13.

The distal end of the light-receiving optical fiber 12 is disposed at the distal end surface of the insertion section 20, and the proximal end of the light-receiving optical fiber 12 is connected to the photodetector 13.

The photodetector 13 photoelectrically converts the observation light L' entering from the light-receiving optical fiber 12 to generate an electric signal corresponding to the intensity of the observation light L' and outputs the generated electric signal to the AD converter 14.

The AD converter 14 samples the electric signal input from the photodetector 13 in synchronization with a sampling signal received from the controller 8 and converts the analog signal to a digital signal, thus obtaining a digital value representing the intensity of the observation light L'. The AD converter 14 transmits the obtained digital value to the image generating unit 3.

The controller 8 generates a control signal and transmits the control signal to the signal generating unit 6. Herein, the controller 8 sets a frequency and an amplitude of the driving signal at which the diameter D of the spot (spot diameter) of the illumination light L on the subject A and the scanning-line pitch P1 of the illumination light L satisfy Conditional Expressions (1) and (1)', and generates a control signal for generating the driving signal having the set frequency and amplitude. Conditional Expressions (1) and (1)' relate to the resolution in the radial direction of the scanning path B:

$$P1 \leq 0.5 \times D. \tag{1}$$

$$0.25 \times D \leq P1. \tag{1}'$$

As shown in FIG. 2, the scanning-line pitch P1 is the distance, in the radial direction, between two substantially circular scanning lines that are adjacent to each other in the radial direction (a direction intersecting the illumination-light scanning direction L) on the spiral scanning path B on the subject A. The scanning-line pitch P1 is determined by the frequency of the oscillation of the distal end of the optical fiber 9 and the rate of change of the amplitude. Thus, by controlling the frequency of the driving signal generated by the signal generating unit 6 and the rate of change of the amplitude, the controller 8 can control the actuator 10 such that the scanning-line pitch P1 satisfies Conditional Expressions (1) and (1)'.

Furthermore, the controller 8 generates a sampling signal having a certain sampling frequency and transmits the sampling signal to the AD converter 14. The controller 8 generates a sampling signal having a sampling frequency with which the spot diameter D of the illumination light L on the subject A and the sampling pitch P2 satisfy Conditional Expressions (2) and (2)'. Conditional Expressions (2) and (2)' relate to the resolution in the circumferential direction of the scanning path B.

$$P2 \leq 0.5 \times D \quad (2)$$

$$0.25 \times D \leq P2 \quad (2)'$$

As shown in FIG. 2, the sampling pitch P2 is the distance between sampling points (the positions irradiated with the illumination light L when the electric signal of the observation light L' is sampled by the AD converter 14) that are adjacent to each other in the circumferential direction (the scanning direction of the illumination light L) on the scanning path B. The sampling pitch P2 is determined by the sampling frequency with which the electric signal is sampled by the AD converter 14. Thus, by controlling the sampling frequency, the controller 8 can control the AD converter 14 such that the sampling pitch P2 satisfies Conditional Expressions (2) and (2)'.

Figure 8:
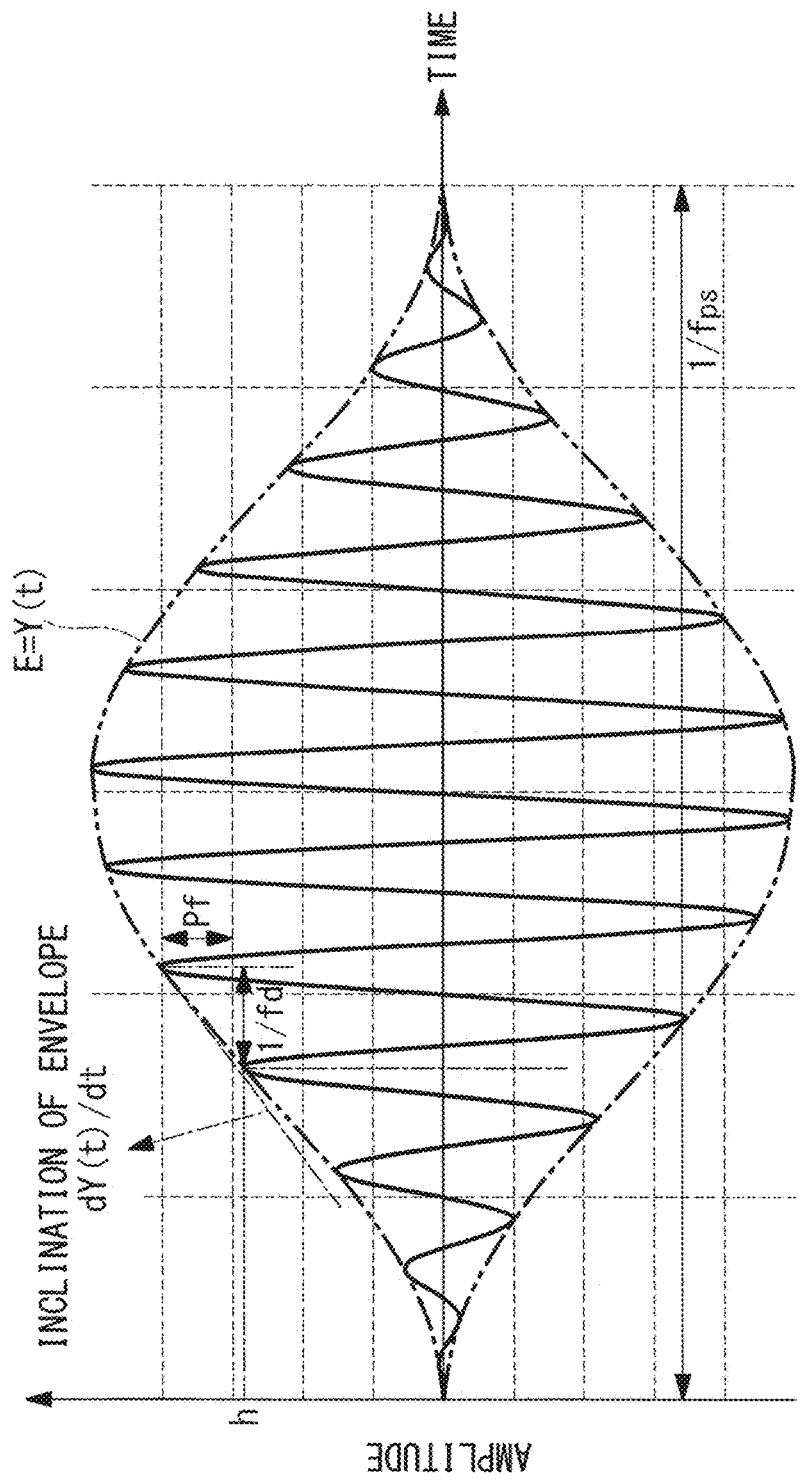
FIG. 8 is a diagram showing a time-series change of the amplitude of the distal end of the optical fiber, the change occurring along a sinusoidal envelope.

Herein, the driving signal is assumed to have a waveform having sinusoidal envelopes, as shown in, for example, FIG. 8. If the controller 8 changes the frequency of an amplitude modulating wave while fixing the driving frequency fd, the number of scanning circulations N per frame changes, and the scanning pitch P1 in the radial direction also changes. Meanwhile, also if the controller 8 changes the driving frequency fd while fixing the frequency of the amplitude modulating wave, the number of scanning circulations N changes, thus making it possible to change the scanning pitch P1 in the radial direction. Furthermore, when the controller 8 changes the amplitude of the driving signal fd while fixing the number of scanning circulations N, the size of the scanning area changes, and, also in this case, the scanning pitch P1 in the radial direction can be changed. Furthermore, if the controller 8 changes the driving frequency fd while fixing the sampling frequency fs of the photodetector 13, the scanning speed in the circumferential direction changes, and thus, the sampling pitch P2 in the circumferential direction can be changed.

As described above, by appropriately setting the driving frequency, amplitude, and the like of the driving signal with the controller 8, the pitches P1 and P2 on the subject can be controlled.

The spot diameter D of the illumination light L on the subject A is determined by the optical properties of optical systems, such as the optical fiber 9 and the scanning lens system 11, through which the illumination light L passes, and the distance between the scanning lens system 11 and the subject A. Because the distance between the scanning lens system 11 and the subject A is substantially uniform in observation using the scanning endoscope system 100, the spot diameter D can be regarded as a fixed value.

The controller 8 calculates, from the control signal, the position on the subject A irradiated with the illumination light L by the optical scanning unit 5 when the AD converter 14 samples the electric signal according to the sampling signal, and transmits information about the calculated irradiation position to the image generating unit 3.

The image generating unit 3 generates a two-dimensional image of the subject A by associating the digital value received from the AD converter 14 with the information about the irradiation position of the observation light L' received from the controller 8. The image generating unit 3 transmits the generated image to the display 4 for display.

The image generating unit 3 and the controller 8 are formed of, for example, a general-purpose or dedicated computer. More specifically, the computer includes: a central processing unit (CPU); a main storage device, such as a RAM; and a sub-storage device, such as a hard disk that stores a control program and an image generating program. By loading the control program from the sub-storage device to the main storage device and executing the program, the CPU realizes the processing by the controller 8. By loading the image generating program from the sub-storage device to the main storage device and executing the program, the CPU realizes the above-described processing by the image generating unit 3 according to the image program.

Next, the operation of thus-configured optical scanning apparatus 1 and the scanning endoscope system 100 according to this embodiment will be described.

When the inside of the body of a patient is to be observed with the scanning endoscope system 100 according to this embodiment, the insertion section 20 is inserted into the body, and the distal end of the insertion section 20 is made to face the living tissue, serving as the subject A. This way, the illumination light L is radiated from the distal end 9a of the optical fiber 9 on the subject A. At this time, the actuator 10 spirally oscillates the distal end 9a of the optical fiber 9, so that the illumination light L is spirally scanned on the subject A.

The observation light L' generated at the irradiation position of the illumination light L is received by the distal end of the light-receiving optical fiber 12, and the photodetector 13 detects the intensity of the observation light L'. Then, the AD converter 14 obtains the digital value of the intensity of the observation light L'. The obtained digital value is transmitted to the image generating unit 3. The image generating unit 3 generates an image by storing the digital value received from the AD converter 14 and the irradiation position of the illumination light L received from the controller 8 in an associated manner. The formed image is displayed on the display 4.

Herein, the relationship between the spot diameter D of the illumination light L and the pitches, i.e., the scanning-line pitch P1 and sampling pitch P2, will be described.

Figure 3A:
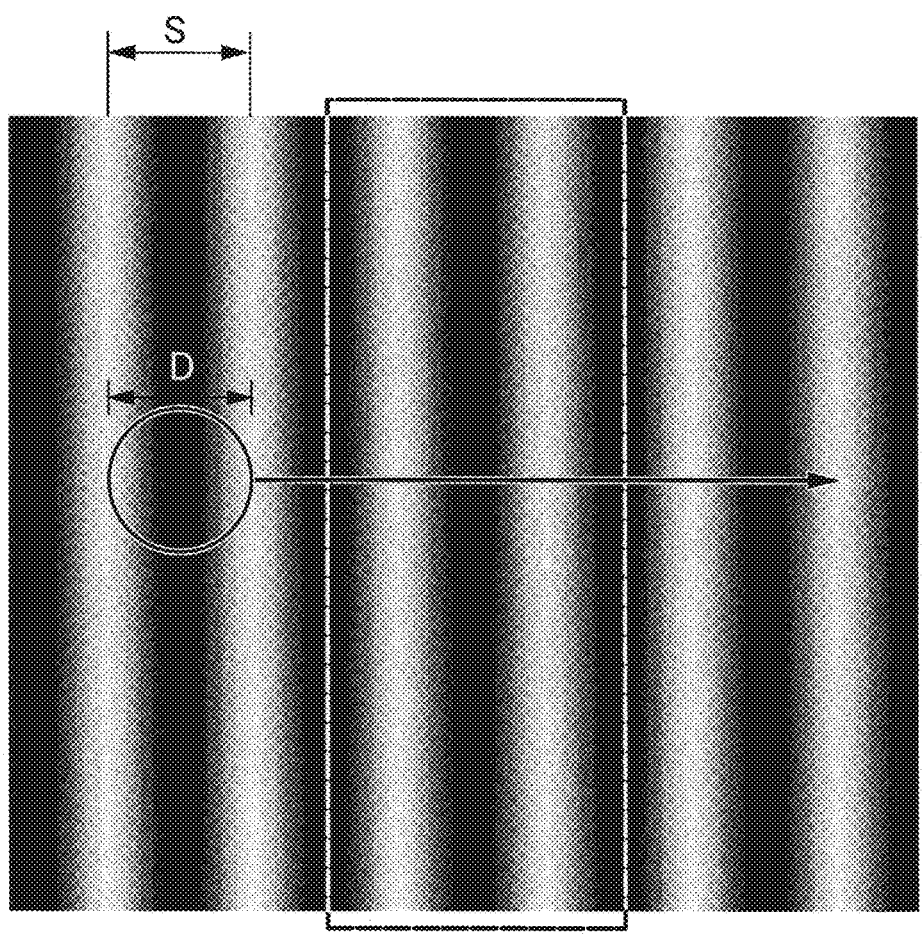
FIG. 3A is a diagram for explaining the relationship between the spot diameter of the illumination light and the resolution.
Figure 4:
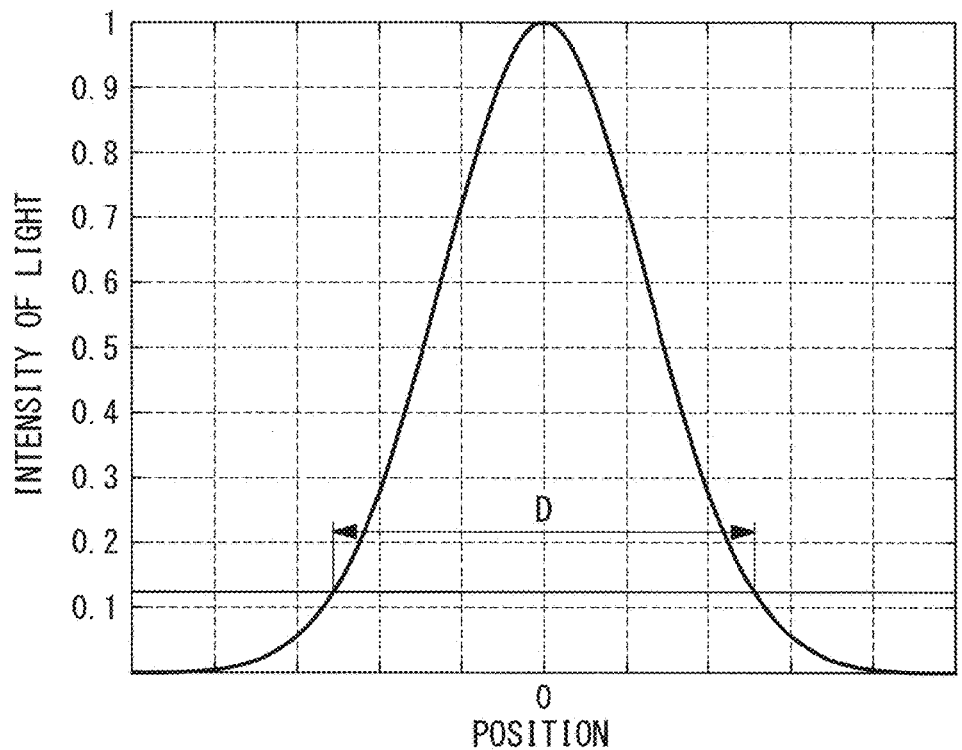
FIG. 4 is a diagram showing the change in the intensity of the illumination light at a cross section of the beam.

A case where the illumination light L with the spot diameter D is scanned over a chart having a black-and-white stripe pattern having a pitch S, as shown in FIG. 3A, is considered. As shown in FIG. 4, the spot diameter D is the Gaussian spot diameter when the illumination light L is assumed to have an intensity according to the Gaussian distribution. In general, a Gaussian spot diameter is defined as the beam width at which the intensity is $1/e^2$ of the maximum intensity.

FIG. 3B shows the intensity of the reflected light of the illumination light L obtained from the chart when the spot diameter D and the pitch S are equal (that is, the spatial frequency of the chart is 1/D). FIG. 3B shows changes in the intensity of the reflected light obtained when the illumination light L is scanned in the direction of the arrow in the area enclosed by a rectangle in FIG. 3A. The vertical axis in FIG. 3B shows the intensity of the reflected light whose maximum intensity is normalized as 1. As shown in FIG. 3B, the intensity of the reflected light varies with the irradiation position of the illumination light L, and the contrast of the intensity of the reflected light is expressed by (Imax−Imin)/(Imax+Imin). Imax is the maximum value of the intensity of the reflected light, and Imin is the minimum value of the intensity of the reflected light. In the example in FIG. 3B, the contrast is calculated to be approximately 30%.

Figure 5:
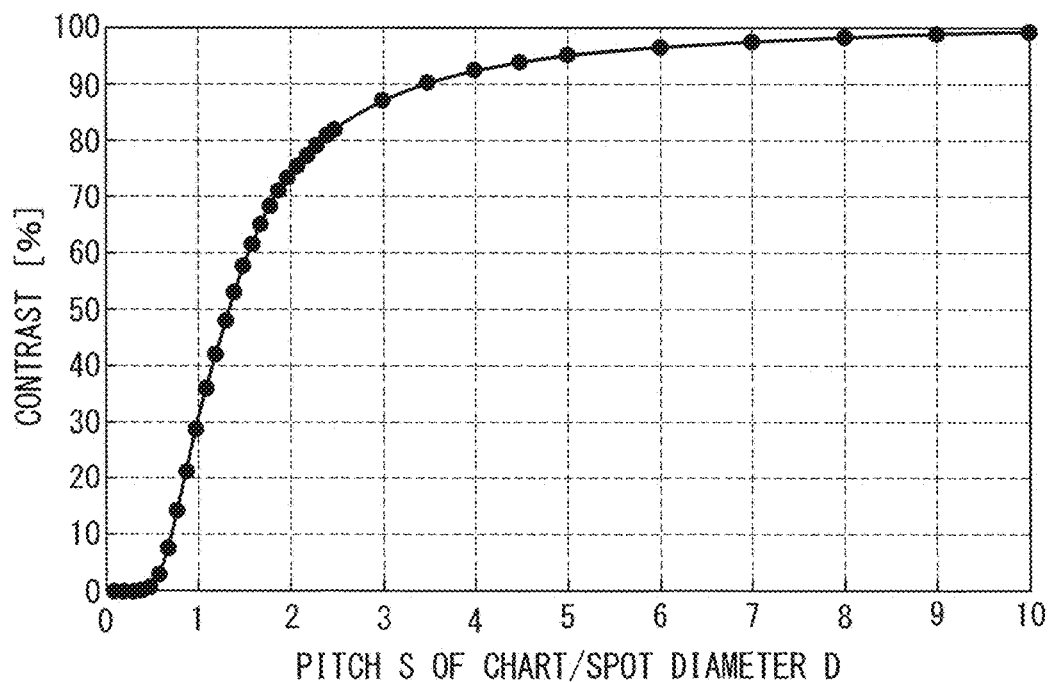
FIG. 5 is a graph showing the relationship between the ratio of the pitch of the chart and the spot diameter of the illumination light (horizontal axis), and the contrast of the intensity of the reflected light (vertical axis).

FIG. 5 shows the calculation result of the contrast of the intensity of the reflected light when the proportion of the pitch S in the spot diameter D (S/D) is changed. As can be seen from FIG. 5, when S=D×2 (that is, the spatial frequency of the chart is 0.5/D), the contrast is 74%, and the stripe pattern of the chart can be fully resolved. When S=D×0.5 (that is, when the spatial frequency of the chart is 2/D), the contrast is 1% or less, and the stripe pattern of the chart cannot be resolved. If the lower limit of the contrast required to resolving the stripe pattern of the chart is set to 30%, the resolution limit is reached when the pitch S is equal to the spot diameter D (that is, when the spatial frequency of the chart is 1/D).

Herein, to reproduce a stripe pattern of a chart having a spatial frequency 1/D and arranged in the radial direction of the scanning path B the scanning-line pitch P1 needs to be 0.5D or less (the spatial frequency needs to be 2/D or more), based on the sampling theorem (sampling theorem). Thus, by setting the scanning-line pitch P1 to 0.5D or less, a pattern having a minimum radial pitch that is theoretically resolvable with the illumination light L having the spot diameter D can be reproduced with 30% contrast in an image.

If the scanning-line pitch P1 is further reduced to less than 0.5D, it is possible to reproduce up to a spatial frequency corresponding to a chart in which S=2× P1, based on the sampling theorem. At this time, information of the spatial frequency when S=1×D or less can also be obtained with 30% or less contrast. However, when S=0.5×D, the contrast is 1% or less. This shows that reducing the scanning-line pitch P1 to less than 0.25×D will not contribute to a further improvement in resolution, but will wastefully increase the number of scanning cycles of the illumination light L and the number of times the observation light L' is sampled by the AD converter 14. Accordingly, the scanning-line pitch P1 is desirably 0.25×D or more.

For the same reason as the scanning-line pitch P1, by controlling the sampling pitch P2 to be from 0.25D to 0.5D, a pattern having a minimum pitch in the circumferential direction of the scanning path B that is theoretically resolvable with the illumination light L having the spot diameter D can be reproduced with 30% contrast in an image.

The resolution of the image obtained with the optical scanning apparatus 1 depends not only on the scanning-line pitch P1 and the sampling pitch P2, but also on the relationship between the spot diameter D of the irradiation light L and the pitches P1 and P2. In this embodiment, the actuator 10 is controlled such that the scanning-line pitch P1 satisfies Conditional Expressions (1) and (1)' with respect to the spot diameter D, and the AD converter 14 is controlled such that the sampling pitch P2 satisfies Conditional Expressions (2) and (2)' with respect to the spot diameter D. This is advantageous in that the optical scanning apparatus 1 using the illumination light L with the spot diameter D can fully exert the potential resolving power thereof, and it is possible to capture high-resolution images.

In this embodiment, the controller 8 may control the actuator 10 so as to additionally satisfy Conditional Expression (3). In Conditional Expression (3), Pf is the scanning pitch of the distal end 9a of the optical fiber 9, and d is the core diameter of the optical fiber 9.

$$P1=D/d \times Pf \quad (3)$$

Based on Conditional Expression (1), Conditional Expression (3) can also be expressed as below:

$$Pf \leq 0.5 \times d. \quad (3)$$

The scanning pitch Pf is a pitch (the distance between two points, which corresponds to two sampling points adjacent to each other in the radial direction or the circumferential direction on the oscillation path) of the distal end 9a of the optical fiber 9 in the radial direction or the circumferential direction.

Figure 6:
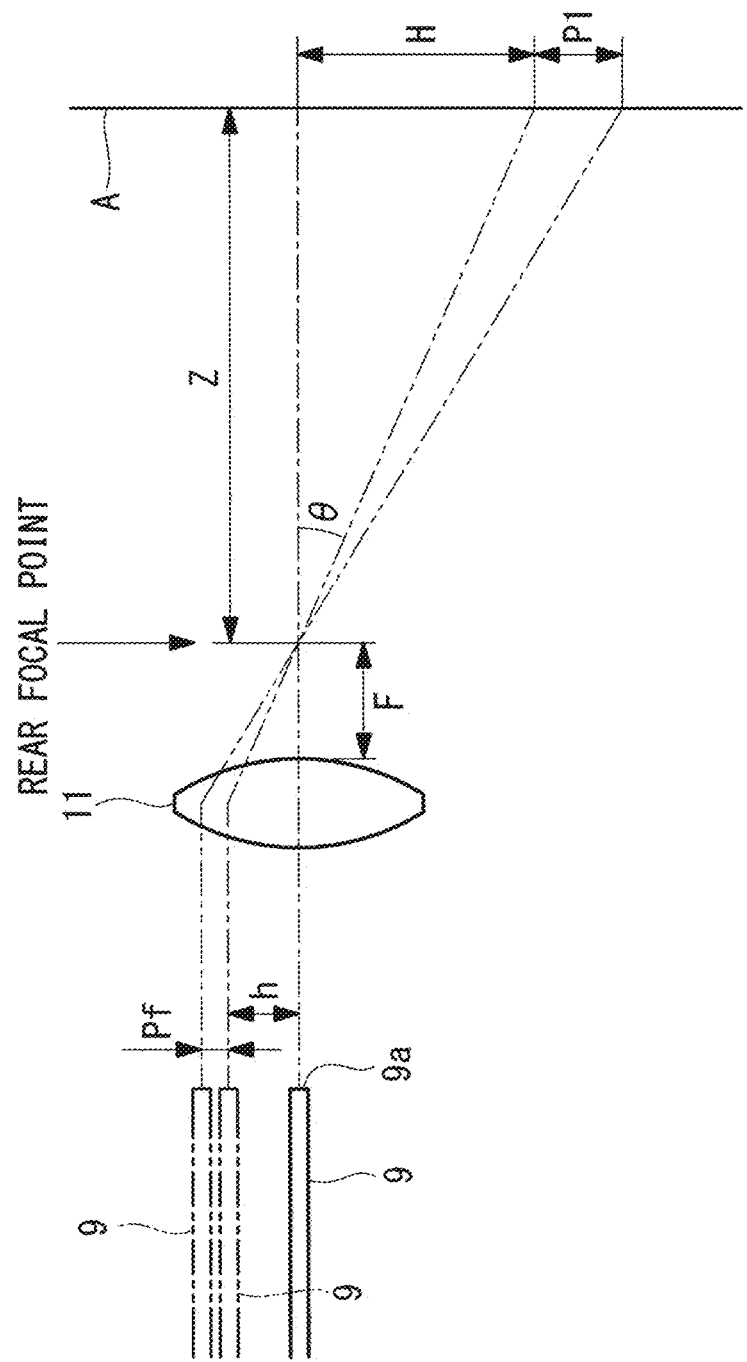
FIG. 6 is a diagram for explaining Conditional Expression (3).

FIG. 6 is a diagram for explaining Conditional Expression (3). A wide-angle lens system having a large angle-of-view is used as the scanning lens system 11 of the optical scanning apparatus 1 for the scanning endoscope system 100. In practice, the distal end portion of the optical fiber 9 oscillated by the actuator 10 performs bending vibration. However, because the amplitude of the distal end 9a of the optical fiber 9 is smaller than the length of the distal end portion of the optical fiber 9, the displacement of the distal end portion of the optical fiber 9 caused by the oscillation is regarded as a parallel movement in the radial direction, as shown in FIG. 6. Accordingly, the principal ray of the illumination light L incident on the scanning lens system 11 on the optical fiber 9 side of the scanning lens system 11 can be approximated as telecentric.

In this case, the amplitude h of the distal end 9a of the optical fiber 9 and the amplitude H of the illumination light L on the subject A are expressed by the expressions below by using the scanning angle θ of the illumination light L. Herein, F is the focal distance of the scanning lens system 11, and the object distance Z is the distance between the rear focal position of the scanning lens system 11 and the subject A.

$$h=F \times \sin \theta$$

$$H=Z \times \tan \theta$$

Hence, the scanning-line pitch P1 and the scanning pitch Pf of the distal end 9a of the optical fiber 9 in the radial direction satisfy Relational Expression (3)' below:

$$\beta=P1/Pf=H/h=Z/(F \times \cos \theta) \quad (3)'$$

where β is the optical magnification.

From Conditional Expressions (1) and (3)', Expression (3)'' below holds:

$$Pf \leq 0.5 \times F/Z \times D \times \cos \theta. \quad (3)''$$

Herein, the spot diameter D varies with the scanning angle θ, and when the spot diameter on the axis (θ≈0°) is $D_0$, an approximation that the spot diameter $D=D_0/\cos \theta$ is possible. Accordingly, Expression (3)'' can be expressed as below:

$$Pf \leq 0.5 \times F \times D_0/Z = 0.5 \times g(Z). \quad (3)''$$

Figure 11:
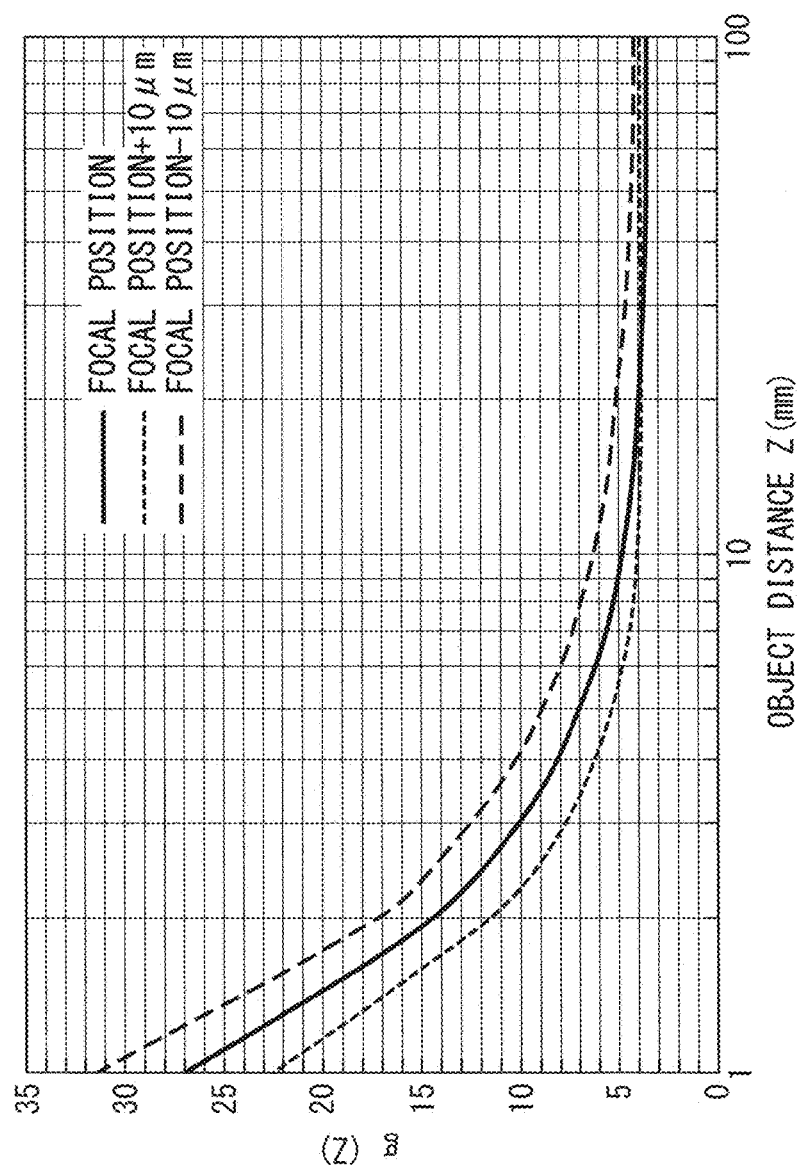
FIG. 11 is a graph showing a function g(Z) for explaining Conditional Expressions (3) and (4).

The axial beam diameter $D_0$ varies with the object distance Z. FIG. 11 shows the result of calculating a function g(Z). To minimize the beam spot diameter of the illumination light L for increased resolution, the distal end 9a of the optical fiber 9 is located at the front focal position of the scanning lens system 11. Note that, as shown in FIG. 11, regardless of the position of the distal end 9 of the optical fiber 9, the value of the function g(Z) is greater than the core diameter d of the optical fiber 9. Accordingly, Expression (3) is derived from Expression (3)''. By satisfying Expression (3), the resolution can be increased regardless of the object distance Z.

For the similar reasons, the expression below is derived.

$$0.25 \times d \leq Pf$$

The reason why the function $g(Z)=F \times D_0/Z \geq d$ holds as in FIG. 11 will be explained below.

Based on Gaussian beam theory, when the distal end 9a of the optical fiber 9 is located near the front focal position of the scanning lens system 11, the beam waist is located near the rear focal position. At this time, the beam waist diameter $\omega_0$ is expressed by the expression below:

$$\omega_0 = 4\lambda F/\pi d$$

where $\lambda$ is the wavelength of the laser beam.

Furthermore, based on Gaussian beam theory, the axial spot diameter $D_0$ at a position a distance Z away from the rear focal position is expressed by the expression below:

$$D_0 = \omega_0 \times \{1 + (Z/Z_R)^2\}^{1/2}$$

where $Z_R = \pi\omega_0^2/4\lambda$.

From these two expressions, $$D_0 = \{(4\lambda F/\pi d)^2 + (d/F)^2 \times Z^2\}^{1/2}.$$

Hence, the function g(Z) is expressed as:

$$g(z) = f \times \{(4\lambda f/\pi dz)^2 + (d/f)^2\}^{1/2}$$

Where $Z_{\to\infty}$, $g(Z) \approx d$. Hence, $g(Z) \geq d$ holds.

As described above, the optimum pitches P1, P2, and Pf depend also on the core diameter d of the optical fiber 9. By satisfying Conditional Expression (3), the optical scanning apparatus 1 can more effectively exert the potential resolving power thereof, and it is possible to capture higher resolution images.

Furthermore, in this embodiment, it is desirable that the controller 8 control the actuator 10 so as to satisfy Conditional Expression (5) or (7), in addition to Conditional Expression (3). In Conditional Expressions (5) and (7), N is the number of scanning cycles of the illumination light L on the scanning path B (the number of circles when the scanning path B is approximated as a collection of concentric circles), and hmax is the maximum amplitude of the distal end 9a of the optical fiber 9.

$$Pf = h\max/N \tag{5}$$

$$Pf \leq \pi/2 \times h\max/N \tag{7}$$

In a scanning method in which the illumination light L is spirally scanned, the shape of the envelopes of the driving signal can be linear or sinusoidal.

Figure 7:
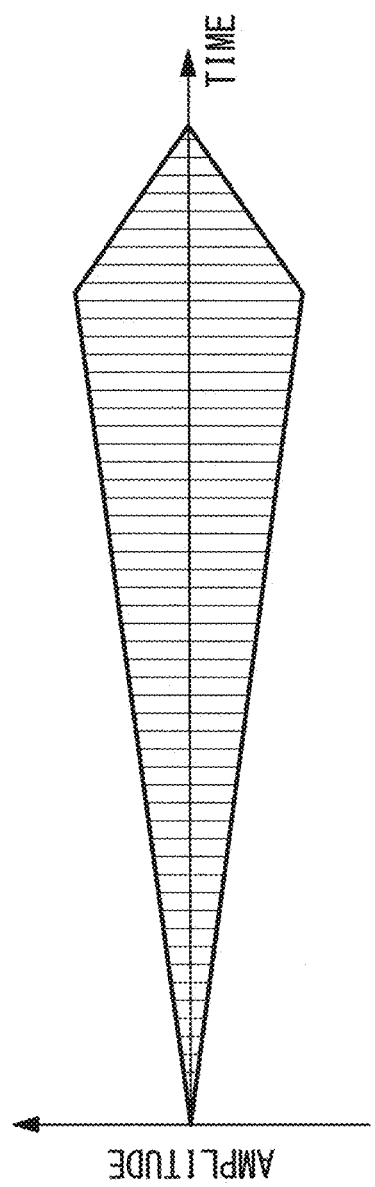
FIG. 7 is a diagram showing a time-series change of the amplitude of the distal end of an optical fiber, the change occurring along a linear envelope.

When the envelopes of the driving signal are linear, the amplitude of the distal end 9a of the optical fiber 9 in the X direction or the Y direction changes linearly with time, as shown in FIG. 7. In this case, the controller 8 controls the actuator 10 so as to satisfy Conditional Expression (5). Conditional Expression (5) is derived because the scanning pitch Pf in the spiral oscillation path of the distal end 9a of the optical fiber 9 is uniform.

On the other hand, when the envelopes of the driving signal are sinusoidal, the amplitude of the distal end of the optical fiber 9 in the X direction or the Y direction changes sinusoidally with time, as shown in FIG. 8. In this case, the controller 8 controls the actuator 10 so as to satisfy Conditional Expression (7). When the amplitude of the distal end 9a of the optical fiber 9 is half of the maximum amplitude, the scanning pitch Pf is maximum, and the resolution is minimum. Conditional Expression (7) defines the resolution with the maximum scanning pitch $Pf = (\pi/2) \times h\max/N$.

As has been described, based on Conditional Expression (5) or (7), it is possible to set the optimum number of circulations N and the maximum amplitude hmax with which the optical scanning apparatus 1 can more effectively exert the potential resolving power thereof, and it is possible to capture even higher resolution images.

Regarding Conditional Expression (7), the maximum scanning pitch Pf is derived as follows.

When the amplitudes of the distal end 9a of the optical fiber 9 in the X direction and the Y direction change with time along sinusoidal envelopes E, an amplitude modulation waveform (the function representing the envelopes E) Y(t) of the oscillation of the distal end 9a is expressed by the expression below:

$$Y(t) = h\max/2 \times \{1 - \cos(2\pi f_0 t)\}$$

where hmax is the maximum amplitude of the distal end 9a of the optical fiber 9, and $f_0$ is the frequency of the amplitude modulation waveform of the driving signal.

Where fd is the oscillation frequency of the distal end 9a of the optical fiber 9, the amplitude coordinate $h_x(t)$ of the distal end 9a of the optical fiber 9 in the X direction and the amplitude coordinate $h_y(t)$ of the distal end 9a of the optical fiber 9 in the Y direction are expressed by the expressions below:

$$h_x(t) = Y(t) \times \sin(2\pi fdt)$$

$$h_y(t) = Y(t) \times \cos(2\pi fdt).$$

Herein, when the waveforms of the outgoing and returning driving signal are symmetrical, and when an image is captured only with one of the outgoing and returning driving signal, the number of circulations N is expressed by the expression below:

$$N = fd/2f_{ps} = fd/2f_0$$

where $f_{ps}$ is the frame rate.

The amplitude modulation function Y(t) is differentiated as below:

$$dY/dt = \pi \times h\max \times f_0 \times \sin(2\pi f_0 t).$$

Referring to FIG. 8, the scanning pitch Pf(h) at the fiber object height h is expressed by the expression below:

$$Pf(h) = dY/dt \times 1/fd.$$

From $$h = h\max/2 \times \{1 - \cos(2\pi f_0 t)\},$$

$\sin(2\pi f_0 t)$ is expressed as the expression below, using the fiber object height h:

$$\sin(2\pi f_0 t) = 2/h\max \times \{h \times (h\max - h)\}^{1/2}$$

Thus, the scanning pitch Pf(h) is derived as the expression below:

$$Pf(h) = \pi \times \{h \times (h\max - h)\}^{1/2} \times 1/N.$$

From this expression, the maximum value of the Pf(h) can be derived.

Furthermore, in this embodiment, it is desirable that the controller 8 control the actuator 10 and the photodetector 13 so as to additionally satisfy Conditional Expression (9):

$$Pf \leq 2 \times h\max \times \sin(\pi \times fd/fs). \tag{9}$$

Figure 9:
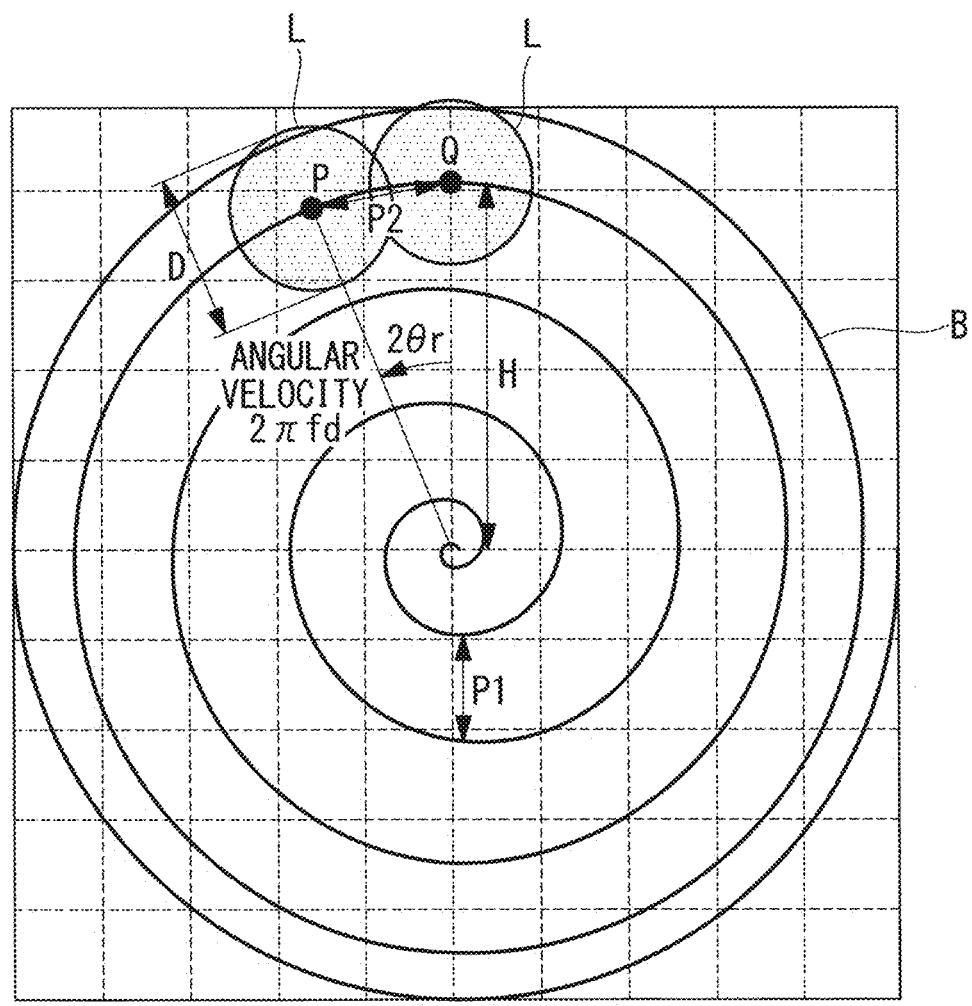
FIG. 9 is a diagram for explaining Conditional Expression (9).

As shown in FIG. 9, the position at which the sampling pitch P2 in the circumferential direction is greatest and thus the resolution is lowest in the scanning path B is on the radially outermost scanning line. Conditional Expression (9) defines the condition for obtaining a high resolution even on the radially outermost scanning line. By setting the frequency (the oscillation frequency of the distal end 9a of the optical fiber 9) fd and the sampling frequency fs of the driving signal so as to satisfy Conditional Expression (9), it is possible to obtain a high resolution across the overall area of the scanning path B.

When the distal end 9a of the optical fiber 9 is spirally oscillated at a certain frequency fd, the illumination light L is spirally scanned at a certain angular velocity $2\pi fd$. The sampling pitch P2 between the two sampling points P and Q that are adjacent to each other in the circumferential direction at this time is expressed by the expression below, using the amplitude H of the illumination light L on the subject A:

$$P2 = 2H \times \sin(\pi \times fd/fs). \quad (9)'$$

Herein, the scanning pitch P2 on the subject and the scanning pitch Pf of the distal end 9a of the optical fiber 9 are proportional to the radius of the scanning circle, that is, the amplitude. Hence, the following relational expression holds between the amplitude h of the distal end 9a of the optical fiber 9 and the amplitude H of the illumination light L on the subject:

$$Pf/p2 = h/H.$$

From this relational expression and Expression (9)', Conditional Expression (9) is derived.

Strictly speaking, the sampling pitch P2 between the points P and Q is the length of the arc between sampling points P and Q, and the length of this arc is sufficiently smaller than the amplitude H. In the expression above, the sampling pitch P2 is obtained by approximating the length as the direct distance between the sampling points P and Q.

Herein, when the amplitude modulation waveform is sinusoidal, Expression (7) holds, as described above. Meanwhile, to achieve a high resolution, the scanning pitch Pf of the distal end 9a of the optical fiber 9 needs to satisfy Expression (1). From Expressions (1) and (7), the condition that should be satisfied by the number of circulations N is expressed by the expression below:

$$\pi/2 \times h\max/N \leq 0.5 \times d.$$

By modifying this expression, Expression (8) is obtained:

$$N \geq \pi \times h\max/d. \quad (8)$$

Accordingly, when the amplitude modulation waveform is sinusoidal, it is desirable that the number of circulations N satisfy Conditional Expression (8).

Meanwhile, when the amplitude modulation waveform is linear, Expression (5) holds, as described above. Further, the scanning pitch Pf of the distal end 9a of the optical fiber 9 needs to satisfy Expression (1) to achieve a high resolution. From Expressions (1) and (5), Expression (6) below is derived. Accordingly, when the amplitude modulation wavelength is linear, it is desirable that the number of circulations N satisfy Expression (6) below:

$$N \geq 2 \times h\max/d. \quad (6)$$

Furthermore, to prevent the number of circulations N from becoming excessive, it is desirable to satisfy Expression (6)' below:

$$N \leq 4 \times h\max/d. \quad (6)'$$

Furthermore, regarding the detection sampling frequency fs, Expression (9) is satisfied, as described above. From Expression (9) and Expression (1), the condition that should be satisfied by the detection sampling frequency fs is the expression below:

$$2 \times h\max \times \sin(\pi \times fd/fs) \leq 0.5 \times d.$$

Herein, because $\pi \times fd/fs$ is very small, an approximation that $\sin(\pi \times fd/fs) \approx \pi \times fd/fs$ is possible.

Hence, the expression above is expressed as:

$$2\pi \times h\max \times fd/fs \leq 0.5 \times d,$$

and Expression (10) is derived:

$$fs \geq 4\pi \times h\max/d \times fd. \quad (10)$$

Figure 10:
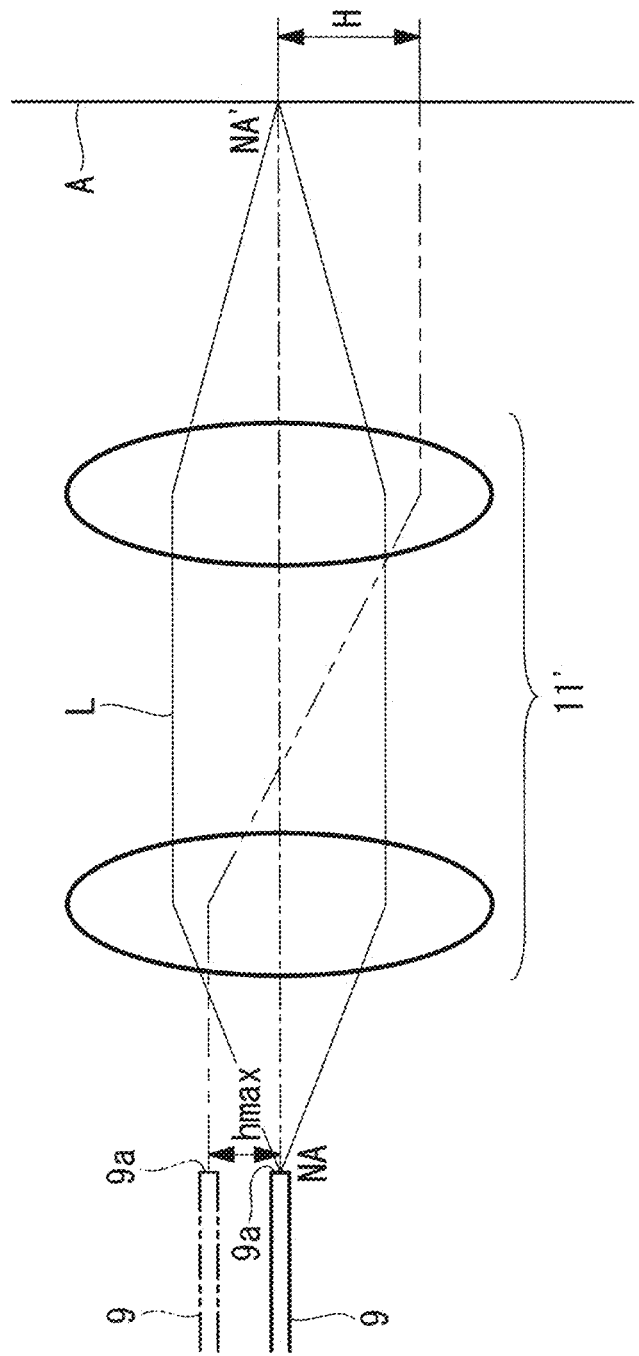
FIG. 10 is a diagram showing a double telecentric scanning lens system, serving as a modification of the scanning lens system of the optical scanning apparatus in FIG. 1.

In this embodiment, although the scanning lens system 11 is telecentric at the optical fiber 9 side, instead, as shown in FIG. 10, the scanning lens system 11 may be telecentric at both the optical fiber 9 side and the subject A side.

This double-telecentric scanning lens system 11' constitutes a confocal optical system. Hence, the optical scanning apparatus having the scanning lens system 11' can be suitably applied to a confocal-scanning microscope.

In the scanning lens system 11' in FIG. 10, the expression below holds, where β is the projection magnification of the scanning lens system 11', NA is the numerical aperture of the optical fiber 9, NA' is the numerical aperture of the illumination light L at the exit side of the scanning lens system 11', and Hmax is the maximum amplitude of the illumination light L on the subject A:

$$Pf/P1 = \beta = H\max/h\max = NA/NA'.$$

Meanwhile, from Gaussian beam optical theory, the spot diameter D is expressed by the expression below by using the wavelength λ. Note that the beam is assumed to be in the far field.

$$NA' = \sin(2\lambda/\pi D)$$

By modifying the expression above, the expression below is obtained. As can be seen from the expression below, in the optical scanning apparatus having the scanning lens system 11', the spot diameter D is determined by the NA of the optical fiber 9 and the projection magnification of the scanning lens system 11'.

$$D = 2\lambda/\pi \times 1/a \sin(NA/\beta)$$

From the expression above and the condition $P1 = \beta \times Pf < 0.5D$, a conditional expression related to the scanning pitch Pf of the distal end 9a of the optical fiber 9 in the double telecentric scanning lens system 11' can be derived. Furthermore, from the scanning pitch Pf and Conditional Expressions (5) to (9), the optimum number of circulations N and the sampling frequency fs can be derived.

In this embodiment, although the illumination light L is scanned along the spiral scanning path B, the method of scanning the illumination light L is not limited thereto, and other scanning methods, such as a raster scanning method or a Lissajous scanning method, may alternatively be used.

Also with another scanning method, by satisfying Conditional Expressions (1), (1)', (2), (2)', (3), and (9), the optical scanning apparatus can fully exert the potential resolving power thereof, and it is possible to capture high-resolution images.

The above-described embodiment leads to the following invention.

An optical scanning apparatus according to a first aspect of the present invention includes: an optical fiber that emits illumination light from a distal end thereof toward a subject; an actuator that oscillates the distal end of the optical fiber; and a controller that controls the actuator so as to two-dimensionally scan the illumination light emitted from the distal end of the optical fiber on the subject. The controller controls the actuator so as to satisfy Conditional Expression (1) below:

$$P1 \leq 0.5 \times D, \quad (1)$$

where D is a spot diameter of the illumination light on the subject, and P1 is a scanning-line pitch of the illumination light on the subject.

According to the first aspect of the present invention, by emitting the illumination light from the distal end of the optical fiber while the distal end of the optical fiber is oscillated by the actuator, the illumination light can be two-dimensionally scanned over the subject.

In this case, the spot diameter D of the illumination light on the subject is a value uniquely determined by the specifications and the design of the optical system, such as the optical fiber. The controller controls the actuator such that the scanning-line pitch P1 satisfies Conditional Expression (1) with respect to the spot diameter D.

Conditional Expression (1) defines the range of the scanning-line pitch P1 necessary to reproduce, in an image, the minimum size that is theoretically resolvable with the illumination light having the spot diameter D in the direction intersecting the illumination-light scanning direction. The scanning-line pitch is the distance between scanning lines adjacent to each other in a direction intersecting the direction in which the illumination light is scanned by the actuator. With this configuration, the potential resolving power that can be obtained with the illumination light having the spot diameter D can be exerted in the direction intersecting the illumination-light scanning direction.

In the first aspect, it is desirable that the controller control the actuator so as to satisfy Conditional Expression (1)' below:

$$0.25 \times D \leq P1. \tag{1}'$$

An optical scanning apparatus according to a second aspect includes: an optical fiber that emits illumination light from a distal end thereof toward a subject; an actuator that oscillates the distal end of the optical fiber; a controller that controls the actuator so as to two-dimensionally scan the illumination light emitted from the distal end of the optical fiber on the subject; and a light detecting unit that detects observation light generated in the subject as a result of the subject being irradiated with the illumination light. The controller controls the light detecting unit so as to satisfy Conditional Expression (2) below:

$$P2 \leq 0.5 \times D, \tag{2}$$

where D is a spot diameter of the illumination light on the subject, and P2 is a sampling pitch of the observation light on the subject.

According to the second aspect of the present invention, the controller controls the light detecting unit such that the sampling pitch P2 satisfies Conditional Expression (2) with respect to the spot diameter D. Conditional Expression (2) defines the range of the sampling pitch P2 necessary to reproduce, in an image, the minimum size that is theoretically resolvable with the illumination light having the spot diameter D in a direction parallel to the illumination-light scanning direction. The sampling pitch is the distance between sampling points (the positions on the subject irradiated with the illumination light at the times when the observation light is detected by the light detecting unit) adjacent to each other in the illumination-light scanning direction. With this configuration, the potential resolving power that can be obtained with the illumination light having the spot diameter D can be exerted in the direction parallel to the illumination-light scanning direction.

In the second aspect, it is desirable that the controller control the light detecting unit so as to satisfy Conditional Expression (2)' below:

$$0.25 \times D \leq P2. \tag{2}'$$

In the second aspect, the controller may control the actuator so as to satisfy Conditional Expressions (1) and (1)' below:

$$P1 \leq 0.5 \times D \tag{1}$$

$$0.25 \times D \leq P1, \tag{1}'$$

where P1 is a scanning-line pitch of the illumination light on the subject.

In the first and second aspects, a scanning lens system that is disposed in front of the distal end of the optical fiber and that focuses the illumination light emitted from the distal end of the optical fiber may be provided, and the controller may control the actuator so as to satisfy Conditional Expression (3) below:

$$P1 = D/d \times Pf, \tag{3}$$

where d is a core diameter of the optical fiber, and Pf is a scanning pitch of the distal end of the optical fiber.

The scanning pitch Pf is the pitch of the distal end of the optical fiber in the circumferential direction or the radial direction. Based on Conditional Expression (3), it is possible to set the optimum scanning pitch Pf with which the potential resolving power that can be obtained with the optical fiber having a core diameter d can be more effectively exerted.

In the second aspect, it is desirable that the controller control the light detecting unit so as to satisfy Conditional Expression (4) below:

$$P2 = D/d \times Pf, \tag{4}$$

where d is a core diameter of the optical fiber, and Pf is a scanning pitch of the optical fiber.

In the first and second aspects, the controller may control the actuator so as to oscillates the distal end of the optical fiber along a spiral path while changing the amplitude thereof with time along linear envelopes and so as to satisfy Conditional Expression (5) below:

$$Pf = h\max/N, \tag{5}$$

where N is the number of circulations in the spiral path, and hmax is the maximum amplitude of the distal end of the optical fiber.

With this configuration, in the method in which the amplitude of the distal end of the optical fiber changes with time at a certain rate of change, it is possible to set, based on Conditional Expression (5), the optimum number of circulations N and the maximum amplitude hmax with which the resolving power can be more effectively exerted.

In the first and second aspects, it is desirable that the controller control the actuator so as to satisfy Conditional Expression (6) below. Furthermore, it is desirable that the controller control the actuator and the light detecting unit so as to satisfy Conditional Expression (6)' below:

$$N \geq 2 \times h\max/d \tag{6}$$

$$N \leq 4 \times h\max/d, \tag{6}'$$

where hmax is the maximum amplitude of the distal end of the optical fiber.

In the first and second aspects, the controller may control the actuator so as to oscillate the distal end of the optical fiber along a spiral path while changing the amplitude thereof with time along sinusoidal envelopes and so as to satisfy Conditional Expression (7) below:

$$Pf \leq \pi/2 \times h\max/N, \tag{7}$$

where N is the number of circulations in the spiral path, and hmax is the maximum amplitude of the distal end of the optical fiber.

With this configuration, in the method in which the amplitude of the distal end of the optical fiber changes with time sinusoidally, it is possible to set, based on Conditional Expression (7), the optimum number of circulations N and the maximum amplitude hmax with which the resolving power can be more effectively exerted.

In the first and second aspects, it is desirable that the controller control the actuator so as to satisfy Conditional Expression (8) below:

$$N \geq \pi \times hmax/d. \tag{8}$$

In the second aspect, the controller may control the actuator and the light detecting unit so as to satisfy Conditional Expression (9) below:

$$Pf \leq 2 \times hmax \times \sin(\pi \times fd/fs), \tag{9}$$

where fs is a sampling frequency of the observation light sampled by the light detecting unit, fd is an oscillation frequency of the distal end of the optical fiber oscillated by the actuator, and hmax is the maximum amplitude of the distal end of the optical fiber.

With this configuration, it is possible to set, based on Conditional Expression (9), the optimum sampling frequency fs with which the resolving power can be more effectively exerted.

In the second aspect, it is desirable that the controller control the actuator and the light detecting unit so as to satisfy Conditional Expression (10) below:

$$fs \geq 4\pi \times hmax/d \times fd. \tag{10}$$

A third aspect of the present invention provides a method of controlling an optical scanning apparatus that spirally scans light emitted from a distal end of an optical fiber on a subject, wherein, in a control step in which an actuator that oscillates the distal end of the optical fiber so as to two-dimensionally scan the illumination light emitted from the distal end of the optical fiber on the subject is controlled, the actuator is controlled so as to satisfy Conditional Expression (1) below:

$$P1 \leq 0.5 \times D, \tag{1}$$

where D is a spot diameter of the illumination light on the subject, and P1 is a scanning-line pitch of the illumination light on the subject.

REFERENCE SIGNS LIST 1 optical scanning apparatus
2 light source
3 image generating unit
4 display
5 optical scanning unit
6 signal generating unit
7 light detecting unit
8 controller
9 optical fiber
10 actuator
11, 11' scanning lens system
12 light-receiving optical fiber
13 photodetector
14 AD converter
20 insertion section
30 control unit body
100 scanning endoscope system

The invention claimed is:

1. An optical scanning apparatus comprising:
   an optical fiber that emits illumination light from a distal end thereof toward a subject;
   an actuator that oscillates the distal end of the optical fiber; and
   a controller that controls the actuator so as to two-dimensionally scan the illumination light emitted from the distal end of the optical fiber on the subject,
   wherein the controller controls the actuator so as to satisfy Conditional Expression (1) below:

$$P1 \leq 0.5 \times D, \tag{1}$$

where D is a spot diameter of the illumination light on the subject, and P1 is a scanning-line pitch of the illumination light on the subject.

2. The optical scanning apparatus according to claim 1, wherein the controller controls the actuator so as to satisfy Conditional Expression (1)' below:

$$0.25 \times D \leq P1. \tag{1'}$$

3. An optical scanning apparatus comprising:
   an optical fiber that emits illumination light from a distal end thereof toward a subject;
   an actuator that oscillates the distal end of the optical fiber;
   a controller that controls the actuator so as to two-dimensionally scan the illumination light emitted from the distal end of the optical fiber on the subject; and
   a light detecting unit that detects observation light generated in the subject as a result of the subject being irradiated with the illumination light,
   wherein the controller controls the light detecting unit so as to satisfy Conditional Expression (2) below:

$$P2 \leq 0.5 \times D, \tag{2}$$

where D is a spot diameter of the illumination light on the subject, and P2 is a sampling pitch of the observation light on the subject.

4. The optical scanning apparatus according to claim 3, wherein the controller controls the light detecting unit so as to satisfy Conditional Expression (2)' below:

$$0.25 \times D \leq P2. \tag{2'}$$

5. The optical scanning apparatus according to claim 3, wherein the controller controls the actuator so as to satisfy Conditional Expression (1) below:

$$P1 \leq 0.5 \times D, \tag{1}$$

where P1 is a scanning-line pitch of the illumination light on the subject.

6. The optical scanning apparatus according to claim 5, wherein the controller controls the actuator so as to satisfy Conditional Expression (1)' below:

$$0.25 \times D \leq P1. \tag{1'}$$

7. The optical scanning apparatus according to claim 1, wherein the controller controls the actuator so as to satisfy Conditional Expression (3) below:

$$P1 = D/d \times pf, \tag{3}$$

where d is a core diameter of the optical fiber, and Pf is a scanning pitch of the optical fiber.

8. The optical scanning apparatus according to claim 3, wherein the controller controls the light detecting unit so as to satisfy Conditional Expression (4) below:

$$P2 = D/d \times pf, \tag{4}$$

where d is a core diameter of the optical fiber, and Pf is a scanning pitch of the optical fiber.

9. The optical scanning apparatus according to claim 7, wherein the controller controls the actuator so as to oscillates the distal end of the optical fiber along a spiral path while changing the amplitude thereof with time along linear envelopes and so as to satisfy Conditional Expression (5) below:

$$Pf = h\max/N, \quad (5)$$

where N is the number of circulations in the spiral path, and hmax is the maximum amplitude of the distal end of the optical fiber.

10. The optical scanning apparatus according to claim 8, wherein the controller controls the actuator so as to oscillates the distal end of the optical fiber along a spiral path while changing the amplitude thereof with time along linear envelopes and so as to satisfy Conditional Expression (5) below:

$$Pf = h\max/N, \quad (5)$$

where N is the number of circulations in the spiral path, and hmax is the maximum amplitude of the distal end of the optical fiber.

11. The optical scanning apparatus according to claim 9, wherein the controller controls the actuator so as to satisfy Conditional Expressions (6) and (6)' below:

$$N \geq 2 \times h\max/d. \quad (6)$$

$$N \leq 4 \times h\max/d. \quad (6)'$$

12. The optical scanning apparatus according to claim 10, wherein the controller controls the actuator so as to satisfy Conditional Expressions (6) and (6)' below:

$$N \geq 2 \times h\max/d. \quad (6)$$

$$N \leq 4 \times h\max/d. \quad (6)'$$

13. The optical scanning apparatus according to claim 7, wherein the controller controls the actuator so as to oscillates the distal end of the optical fiber along a spiral path while changing the amplitude thereof with time along sinusoidal envelopes and so as to satisfy Conditional Expression (7) below:

$$Pf \leq \pi/2 \times h\max/N. \quad (7)$$

14. The optical scanning apparatus according to claim 8, wherein the controller controls the actuator so as to oscillates the distal end of the optical fiber along a spiral path while changing the amplitude thereof with time along sinusoidal envelopes and so as to satisfy Conditional Expression (7) below:

$$Pf \leq \pi/2 \times h\max/N. \quad (7)$$

15. The optical scanning apparatus according to claim 13, wherein the controller controls the actuator so as to satisfy Conditional Expression (8) below:

$$N \geq \pi \times h\max/d. \quad (8)$$

16. The optical scanning apparatus according to claim 14, wherein the controller controls the actuator so as to satisfy Conditional Expression (8) below:

$$N \geq \pi \times h\max/d. \quad (8)$$

17. The optical scanning apparatus according to claim 8, wherein the controller controls the actuator and the light detecting unit so as to satisfy Conditional Expression (9) below:

$$Pf \leq 2 \times h\max \times \sin(\pi \times fd/fs), \quad (9)$$

where fs is a sampling frequency of the observation light sampled by the light detecting unit, fd is an oscillation frequency of the distal end of the optical fiber oscillated by the actuator, and hmax is the maximum amplitude of the distal end of the optical fiber.

18. The optical scanning apparatus according to claim 17, wherein the controller controls the actuator and the light detecting unit so as to satisfy Conditional Expression (10) below:

$$fs \geq 4\pi \times h\max/d \times fd. \quad (10)$$

19. A method of controlling an optical scanning apparatus that spirally scans light emitted from a distal end of an optical fiber on a subject, wherein, in a control step in which an actuator that oscillates the distal end of the optical fiber so as to two-dimensionally scan the illumination light emitted from the distal end of the optical fiber on the subject is controlled, the actuator is controlled so as to satisfy Conditional Expression (1) below:

$$P1 \leq 0.5 \times D, \quad (1)$$

where D is a spot diameter of the illumination light on the subject, and P1 is a scanning-line pitch of the illumination light on the subject.

* * * * *